United States Patent [19]

Nahsner

[11] Patent Number: 5,476,103
[45] Date of Patent: Dec. 19, 1995

[54] APPARATUS AND METHOD FOR ASSESSMENT AND BIOFEEDBACK TRAINING OF LEG COORDINATION AND STRENGTH SKILLS

[75] Inventor: Lewis M. Nahsner, Lake Oswego, Oreg.

[73] Assignee: Neurocom International, Inc., Clackamas, Oreg.

[21] Appl. No.: 74,075

[22] Filed: Jun. 8, 1993

Related U.S. Application Data

[63] Continuation-in-part of Ser. No. 774,553, Oct. 10, 1991, abandoned.

[51] Int. Cl.$^6$ .................................................. A61B 5/103
[52] U.S. Cl. ........................... 128/782; 434/258; 482/902
[58] Field of Search ........................ 128/782, 779, 128/774; 482/52, 51, 53, 54, 133, 901, 902; 73/172; 434/258

[56] References Cited

U.S. PATENT DOCUMENTS

| | | | |
|---|---|---|---|
| 2,043,187 | 6/1936 | Owens | 128/2 |
| 2,095,268 | 10/1937 | Roberts | 73/51 |
| 3,420,222 | 1/1969 | Noe et al. | 128/2 |
| 3,850,034 | 11/1974 | Tsuchiya et al. | 73/172 |
| 3,906,931 | 9/1975 | Terekhov | 128/2 |
| 4,014,398 | 3/1977 | Gresko | 177/208 |
| 4,122,840 | 10/1978 | Tsuchiya et al. | 128/2 S |
| 4,136,682 | 6/1979 | Pedotti | 128/2 S |
| 4,195,643 | 4/1980 | Pratt, Jr. | 128/779 |
| 4,267,728 | 5/1981 | Manley et al. | 73/172 |
| 4,416,293 | 11/1983 | Anderson et al. | 128/782 |
| 4,503,705 | 3/1985 | Polchaninoff | 73/172 |
| 4,813,436 | 3/1989 | Au | 128/779 |
| 4,830,021 | 5/1989 | Thornton | 128/707 |
| 5,050,861 | 9/1991 | Thomas et al. | 272/70 |
| 5,209,240 | 5/1993 | Jain et al. | 128/779 |
| 5,337,757 | 8/1994 | Jain et al. | 128/779 |

FOREIGN PATENT DOCUMENTS

| | | | |
|---|---|---|---|
| 2619702 | 3/1989 | France . | |
| 1507408 | 9/1989 | Russian Federation | 482/52 |
| 589979 | 1/1978 | U.S.S.R. . | |

OTHER PUBLICATIONS

"The Expertvision System," brochure, Motion Analysis Corp., Santa Rosa, Ca., Date unknown, Author unknown.
"CDG—Computer Dyno Graphy," brochure, Infotronic Medical Engineering, Tubbergan, The Netherlands.
"The Two Most Durable Machines in Your Club," brochure, Unisen, Date unknown, Author unknown.

(List continued on next page.)

*Primary Examiner*—Stephen C. Pellegrino
*Assistant Examiner*—Guy V. Tucker
*Attorney, Agent, or Firm*—Bromberg & Sunstein

[57] ABSTRACT

Apparatus and methods for assessing and biofeedback training of movement coordination, strength, and speed skills critical to balance during a mobility task performed by a subject on a combination of surfaces, in particular stepping up and down, climbing and descending stairs, sitting and rising from a sitting position. The apparatus includes a force-sensing plate. The force-sensing plate measures the forces exerted on its sensing area, i.e., its top surface, and transmits output signals representative of the measured forces. A plurality of support surfaces is mounted in specified positions relative to the force-sensing plate's sensing area, in such a way that substantially all forces exerted by the subject onto the support surfaces is transmitted to the sensing area. The plurality of surfaces may form a step, stairs or a seat. A data processor accepts the output signals from the force-sensing plate and calculates quantities related to the positions and magnitudes of forces exerted by the subject on the support surfaces. In order to permit biofeedback training, a display for displaying position and magnitude quantities calculated and for displaying additional quantities related to performance goals is provided so that the subject can see these quantities while performing the mobility task.

31 Claims, 13 Drawing Sheets

OTHER PUBLICATIONS

"Vicon," brochure, Oxford Medilog Systems Limited, Oxfordshire, England, date unknown, Author unknown.

"The Step," model No. 4227E; Superstep, model No. 5638E; catalog, FlagHouse, Inc., Mt. Vernon, New York (Fall 1992), Author unknown.

"Balance Master & Balance Master Trainer," brochure, NeuroCom International, Inc., Clackamas, Oregon (1990), Author unknown.

"Balance System," brochure, Chattecx Corporation, Chattanooga, Tennessee (1991), Author unknown.

"Cybex Extremity Systems," advertisement, Lumex, Inc., Ronkonkoma, New York (1992), Author unknown.

"Lido," advertisement, Loredan Biomedical Inc., West Sacramento, California (1992), Author unknown.

"The Biodex Advantage," advertisement, Biodex Medical Systems Inc., Shirley, New York (1992), Author unknown.

"A Pressure Mapping System for Gait Analysis," Sensors, pp. 21–25 (May 1991) (Author unknown).

Kram et al., "A Treadmill–mounted Force Platform," American Physiological Society, pp. 1692–1698 (1989).

Nashner, L. M., *Sensory Feedback in Human Posture Control*, Massachusetts Institute of Technology Report MVT–70–3 (1970).

Begbie, C. H., "Some problems of postural sway," in: *Symposium on Myotatic, Kinesthetic, and Vestibular Mechanisims*, London, Churchill Ltd, pp. 80–101 (1967).

Herrman, R. "Augmented sensory feedback in the control of limb movement,"in: Fields, W. S., ed., *Neural Organization and Its Relevance to Prosthetics*, Miami, Symposia Specialists, pp. 197–215 (1973).

Wannstedt, G. T., et al., "Use of augmented sensory feedback to achieve symmetrical standing," *Physical Therapy*, vol. 58, pp. 553–559 (1978).

Seeger, B. R., et al., "Biofeedback therapy to achieve symmetrical gait in children with hemiplegic cerebral palsy," *Archives in Physical Medicine and Rehabilitation*, vol. 64, kpp. 160–162 (1983).

Shumway–Cook A., et al., "Postural sway biofeedback: its effect on reestablishing stance stability in hemiplegic patients," *Archives of Physical Medicine and Rehabilitation* 69: 395–400 (1988).

Winstein, C. J., et al., "Standing balance training: effect on balance and locomotion in hemiplegic adults," *Archives of Physical Medicine and Rehabilitation*, vol. 70, pp. 755–762 (1989).

Clarke, A. H., et al., "Posturography with sensory feedback—a useful approach to vestibular training?," in: Brandt, T., et al., eds., *Disorders of Posture and Gait*, Stuttgart, George Thieme Verlag, pp. 281–284 (1990).

Jobst U., "Patterns and strategies in posturographic biofeedback training," in: Brandt, T., et al., eds., *Disorders of Posture and Gait*, Stuttgart, George Thieme Verlag, pp. 277–300 (1990).

Hamann, K. F., et al., "Clinical application of posturography: body tracking and biofeedback training,"in: Brandt, T., et al., eds., *Disorders of Posture and Gait*, Stuttgart, George Thieme Verlag, pp. 295–298 (1990).k Hamman, R. G., et al., "Training effects during repeated therapy sessions of balance training using visual feedback," *Archives of Physical Medicine and Rehabilitation*, vol. 73, pp. 738–744 (1992).

Sackley, C. M., et al., "The use of a balance performance monitor in the treatment of weight–bearing and weight–transference problems after stroke," *Physiotherapy*, vol. 78, pp. 907–913 (1992).

Hoy, M. G., et al., "Effect of age and muscle strength on coordination of rising from a chair," in: Woollacott M. and Horak, F, eds., *Posture and Gait: Control Mechanisms*, Univ. of Oregon Books, pp. 187–190 (1992).

Schultz, A. B., et al., "Biomechanical analyses of rising from a chair,"*Journal of Biomechanics*, vol. 25, No. 12, pp. 1383–1391 (1992).

Riedel, S. A., et al., "An instrumented chair for assessing seated stability," *Journal of Clinical Engineering*, vol. 15, No. 6 (1990).

Arcan, M., et al., "FGP assessment of postural disorders during the process of rehabilitation," *Scand. J. Rehab. Med.*, vol. 9, pp. 165–168 (1977).

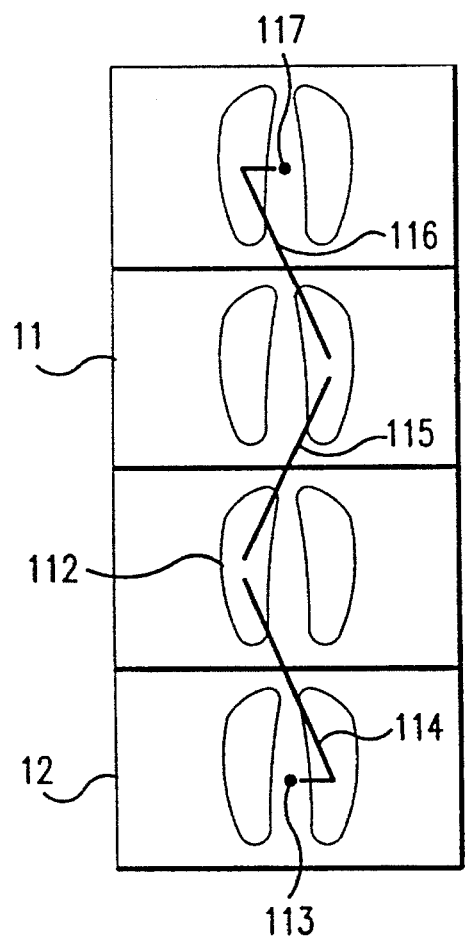 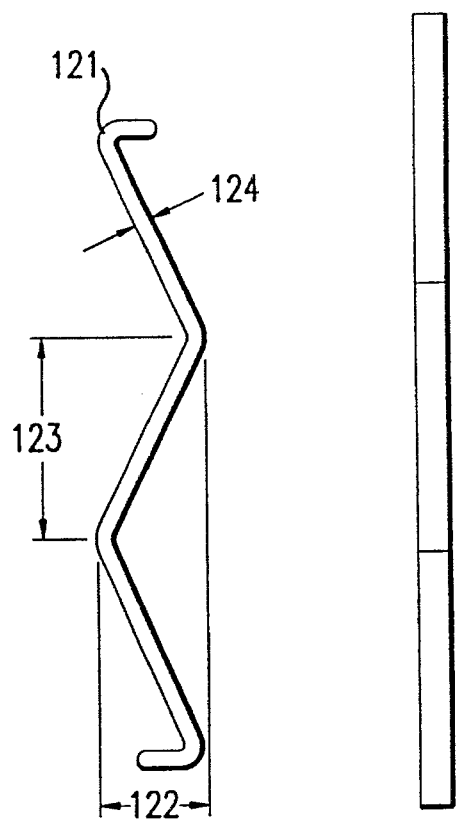
FIG.11　　　FIG.12　　FIG.13

APPARATUS AND METHOD FOR ASSESSMENT AND BIOFEEDBACK TRAINING OF LEG COORDINATION AND STRENGTH SKILLS

DESCRIPTION

This application is a continuation-in-part of Ser. No. 07/774,553 filed on Oct. 10, 1991, now abandoned, which is incorporated herein by reference.

TECHNICAL FIELD

The invention relates to devices and methods for the training and assessment of leg coordination and strength skills critical to balance while stepping, stair climbing, sitting and arising from a seated position.

BACKGROUND OF THE INVENTION

A. Use of Forceplates in Biofeedback Training of Balance

The design and use of forceplates to measure the forces exerted by the feet of a standing subject and the relations between these forces and the subject's balance are well described in the prior art. Examples of these prior art descriptions include: Nashner, L. M., *Sensory Feedback in Human Posture Control*, Massachusetts Institute of Technology Report MVT-70-3 (1970), and Black, F.O., et al., "Computerized screening of the human vestibulospinal system," *Annals of Otology Rhinology and Laryngology*, vol. 87, pp. 783–789 (1978). U.S. Pat. No. 4,136,682 to Pedotti describes a forceplate system on which a standing subject walks, and also includes methods for processing the resulting information relative to the motions of the subject.

The balance of a standing subject is typically characterized in terms of quantities related to the position of the center of force exerted by the feet against the support surface relative to the positions of the feet on the surface. The magnitude and the position of the center of force exerted by a subject standing on a single forceplate, however, is determined in the coordinates of the forceplate support surface. To calculate quantities related to the balance of a subject standing on a single forceplate requires knowledge of the positions of the two feet relative to the forceplate. When the subject is standing with each foot on a separate independent forceplate, the calculation of quantities related to balance requires additional information of the positions of the two forceplates relative to one another.

B. Biofeedback Training of Erect Standing Balance

The earliest known application of a device and method for biofeedback training of erect standing balance was reported in 1967 by Begbie, C. H., "Some problems of postural sway," in: deReuck A. V. S., Knight J., eds. *CIBA Foundation Symposium on Myotatic, Kinesthetic, and Vestibular Mechanisms*, London, Churchill Ltd, pp. 80–101 (1967).

The Begbie study used a compliant platform to monitor postural sway during erect standing. When the standing subject swayed forward, backward, or to one side, the resultant reaction forces between the feet and the platform support surface deflected the surface in the direction of the subject's sway. Deflection was measured using a potentiometer, the output of which provided a signal related to the direction and extent of the subject's sway. Applications for the measurement and biofeedback device described by Begbie, however, were limited to tasks in which the subject performed standing with the feet in fixed positions.

The Begbie report described a biofeedback application of the platform device in which an oscilloscope displayed two quantities to the subject. The first quantity displayed the deflection of the platform, allowing the subject to see the direction and extent of his own swaying. The second quantity was a target sway position providing the subject with a performance goal. The report described how the platform and biofeedback display helped patients with vestibular balance disorders by allowing them to substantially reduce their otherwise abnormal postural sway.

The description of a device and method for training a standing subject to modify the distribution of weight load between the two legs was described in 1973 by Herman, R, "Augmented sensory feedback in the control of limb movement," in: Fields, W. S., ed., *Neural Organization And Its Relevance to Prosthetics*, Miami, Symposia Specialists, pp. 197–215 (1973).

The Herman report described several forms of independent force measuring devices for monitoring the vertical load on each leg. The report further described auditory and visual methods for displaying the distribution of the load to the subject. Biofeedback load displays included a frequency modulated tone signal and an array of independently controlled signal lights. With the audio biofeedback, the frequency of the tone increased or decreased as the load on a selected leg increased or decreased. The pattern of illuminated lights changed to signal changes in leg loading. Like the Begbie device and methods, biofeedback training of loads was limited to tasks in which the subject stood with the feet maintained in fixed positions on the support surface.

The Herman report further described clinical training applications of the leg load devices and methods in which patients with musculoskeletal and neurological disorders were instructed to achieve a desired weight bearing on a selected leg by bring the auditory or visual feedback signal within specified target range.

U.S. Pat. No. 4,122,840 by Tsuchiya et al., entitled "Apparatus for Analyzing the Balancing Function of the Human Body," describes a device and method using biofeedback to train the distribution of loads between the two legs of a standing subject. The device consists of independent vertical load detectors to measure the distribution of loads on the legs and an array of light emitting diodes to visually display actual loads relative to a specified target load signal. With the exception of minor differences in force measuring and display technology, the measurement and biofeedback methods were very similar to those described earlier by Begbie and Herman. Like the Begbie and Herman devices and methods, the Tsuchiya and Ohnishi patent is also limited to standing tasks in which the feet are maintained in fixed positions on a support surface.

C. Other Technologies for Measuring Balance and Movement

A number of technologies in addition to force sensing surfaces are potentially available for calculating and displaying quantities related to performance while an erect standing subject performs movement tasks. Several manufacturers market optically based motion analysis systems which measure subject movements without requiring that the feet be positioned on a force sensing surface. Two examples include the ExpertVision system by MotionAnalysis Corp., Santa Rosa, Calif. and the Vicon system by Oxford Medilog Systems Limited, Oxfordshire, England. These technologies, however, are substantially more expensive than force sensing surfaces. These optical motion analysis technologies are not appropriate for routine clinical training, because they require considerable time and technical expertise to calibrate body mounted position targets.

A second potential technology for measuring quantities related to the performance of a standing subject is the shoe instrumented with force sensing devices. An example of such a system is the Computer Dyno Graph (CDG) marketed by Infotronic Medical Engineering of Tubbergan, The Netherlands. For routine clinical use, this type of system also has the disadvantage of also requiring body mounted hardware and calibration. In addition, since these devices do not include means for determining the positions of the force sensing shoes on a continuous basis, they cannot be used to calculate quantities related to the subject's balance.

D. Clinical Applications of Balance Biofeedback Training

A number of published research reports have described clinical applications for balance training devices in accordance with the original concepts described by Begbie and Herman. Balance training was used to achieve symmetrical standing in stroke patients. Wannstedt, G. T., et al., "Use of augmented sensory feedback to achieve symmetrical standing," Physical Therapy, vol. 58, pp. 553–559 (1978). Similar devices were used to train children with cerebral palsy. Seeger, B. R., et al., "Biofeedback therapy to achieve symmetrical gait in children with hemiplegic cerebral palsy," *Archives of Physical Medicine and Rehabilitation*, vol. 64, pp. 160–162 (1983). Two additional studies used balance biofeedback therapy to reestablish the stability of stance and gait in hemiplegic patients. Shumway-Cook, A., et al., "Postural sway biofeedback: its effect on reestablishing stance stability in hemiplegic patients," *Archives of Physical Medicine and Rehabilitation* 69:395–400 (1988); and Winstein, C. J., et al., "Standing balance training: effect on balance and locomotion in hemiplegic adults," *Archives of Physical Medicine and Rehabilitation*, vol. 70, pp. 755–762 (1989). Additional studies using biofeedback training in standing patients include: Clarke, A. H., et al., "Posturography with sensory feedback—a useful approach to vestibular training?," in: Brandt, T., et al., eds., *Disorders of Posture and Gail*, Stuttgart, George Thieme Verlag, pp. 281–284 (1990); Jobst U., "Patterns and strategies in posturographic biofeedback training," in: Brandt, T., et al., eds., *Disorders of Posture and Gait*, Stuttgart, George Thieme Verlag, pp. 277–300; Hamann, K. F., et al., "Clinical application of posturography: body tracking and biofeedback training," in: Brandt, T., et al., eds., *Disorders of Posture and Gait*, Stuttgart, George Thieme Verlag, pp. 295–298 (1990); and Hamman, R. G., et al., "Training effects during repeated therapy sessions of balance training using visual feedback," *Archives of Physical Medicine and Rehabilitation*, vol. 73, pp. 738–744 (1992).

The most recent clinical study is Sackley, C. M., et al., "The use of a balance performance monitor in the treatment of weight-bearing and weight-transference problems after stroke," *Physiotherapy*, vol. 78, pp. 907–913 (1992). This article describes clinical applications of a system comprised of two independent force-measuring footplates. The article describes training tasks in which the patient stands in-place on the footplates, rises from a chair onto the footplates, and transfers weight between two footplates, one at floor level and the other on a higher step surface.

While the Sackley, et al., article is the first to describe the measurement and biofeedback display of leg loading information during weight transfers to different step heights and during rises from a chair, the described devices and methods cannot measure or display quantities related to the subject's balance during performance of these tasks. This is because the device does not include means for calculating the position of the center of force relative to the positions of the two feet. Specifically, the operations leading to calculation of the display quantities do not take into account the positions of the feet on the footplates or the positions of the footplates.

The Sackley, et. al., device and methods do not permit the calculation and biofeedback display of quantities related to balance during the sit to stand movement. Because the device does not include means for measuring the forces exerted by the buttocks against the seat surface, quantities related to the subject's balance cannot be calculated when a portion of the subject's weight is supported by the chair surface. Additionally, the operations leading to calculation of the display quantities do not take into account the positions of the footplates relative to the chair surface.

E. Equipment for Balance Biofeedback and Mobility Training

A number of manufacturers market equipment to train patients in standing movement tasks which reproduce daily life functions. Clinical equipment of this type includes adjustable height steps for the training of stepping and stair climbing, for examples: The Step, model number 4227E; Superstep, model number 8362E; One-Sided Stairs, model number 5638E, all marketed by FlagHouse, Inc., Mt. Vernon, N.Y. Currently marketed products for exercising lifelike standing tasks, however, do not incorporate the means to measure or display quantities related to the balance performance of subjects or to provide subjects with performance goals.

Several manufactures now market devices for the assessment and biofeedback training of weight bearing and balance while patients stand erect with the feet maintained in fixed positions on a support surface. In the United States for example, the Balancemaster system manufactured by NeuroCom International, Inc. of Clackamas, Oreg. uses signals from a forceplate to calculate the position of the subject's body center of gravity (COG) over the feet. The COG is displayed on a video monitor along with one or more position targets selected by the clinician. When operating in the training mode, the subject is instructed to shift body position to move the COG into one or a sequence of several targets. In the assessment mode, the speed and accuracy with which the subject moves the COG to targets are calculated.

The Balance System manufactured by Chattecx division of Chattanooga Corporation of Chattanooga, Tenn. uses four vertical force measuring plates to determine the percentage of body weight carried by the front and back portions of each foot. The feedback display and training operations of the device are similar to the NeuroCom system in that a single target indicating the position of the body weight relative to the feet is displayed on a video monitor relative to additional targets.

The Balance Performance Monitor (BPM) is manufactured by SMS Healthcare, Essex CM19 5TL, England. The system consists of two force-measuring footplates and a visual display. Each footplate measures total weight as well as the front-back distribution of the weight. The footplates are movable and can be placed at different locations or surfaces of different heights. The computational means, however, determines only the distribution of weight between the two footplates, independent of the positions of the two plates. Thus, the system does not include computational means to calculate and display quantities related to the balance of the subject under a variety of task conditions.

A number of manufacturers have market devices for assessing and training the strength and range of motion about selected joint of both the arms and legs. The Cybex Extremity Systems manufactured by Cybex division of Lumex, Inc., of Ronkonkoma, N.Y., measures and displays to the subject torsional forces exerted by a number of extremity joints including the ankle, knee, and hip. Forces can be measured as the subject exerts effort against an immovable load (isometric) and while the joint moves a constant velocity (isokinetic). Similar extremity strength training systems are marketed as the Kintron multijoint system by the Chattanooga Group, Inc., of Hixon, Tenn. the Lido Active Multijoint by Loredan Biomedical Inc., of West Sacramento, Calif., and the Biodex Multi-joint Strength Training System by Biodex Medical Systems Inc., of Shirley, N.Y. While all of these systems allow joint strength assessment and training during active movements, none are able to assess and train performance in standing, weight bearing tasks, and none are able to assess and train coordination and strength skills related to balance.

A number of research reports have described chairs instrumented with force measuring devices to quantify the forces associated with sitting and rising from a chair. The earliest known study used forceplates to analyze forces at the knee during the rising movement, Ellis, M. I., et al., "Forces in the knee joint whilst rising from normal and motorized chairs," *Engineering Medicine*, vol. 8, pp. 33–40 (1979). More recent reports have placed forceplates on both the chair and the floor and have also used motion analysis systems to characterize all of the forces and motions; for example, Alexander, N. B., et al., "Rising from a chair: effects of age and functional ability on performance biomechanics," *Journal of Gerontological Medicine*, vol. 46, pp. 91–98 (1991). These research devices, however, were not designed to allow the biofeedback training of patients performing sitting and rising movements from a chair.

F. Summary of Background Art

The use of force measuring surfaces to calculate the distribution of forces exerted by the feet relative to the base of support and the biofeedback display of these quantities to train aspects of balance during erect standing with the feet maintained in fixed positions is well established in the prior art. The prior art includes: (1) numerous clinical studies demonstrating applications for balance training with biofeedback and (2) several manufacturers with devices for the biofeedback training of standing in-place balance.

Biofeedback training devices based on forceplate measuring systems available in the present art, however, are useful primarily when the patient performs with the feet maintained in fixed positions. It is possible to use optical motion analysis technology to calculate quantities related to a subject's balance during standing movement tasks such as stepping, stair climbing, and sitting and rising from a chair without requiring the feet be maintained in fixed positions. These optical motion analysis technologies, however, are expensive and require highly technical setup and calibration procedures which are too complex for use in mainstream clinical training applications.

Biofeedback training products are also available in the present art for the assessment of extremity strength during active limb movements. None of these products, however, allow assessment and training of coordination and strength skills when the leg is in the standing weight bearing condition, and none permit training of these skills in relation to balance.

DESCRIPTION OF THE INVENTION

The invention provides apparatuses and methods for assessing and biofeedback training of movement coordination, strength, and speed skills critical to balance during a mobility task performed by a subject on a combination of surfaces. The apparatus includes a force-sensing means, for example, a force-sensing plate. The force-sensing plate measures the forces exerted on its sensing area, which is typically most of its top surface, and transmits output signals representative of the measured forces. A plurality of support surfaces is mounted in specified positions relative to the force-sensing plate's sensing area, in such a way that substantially all forces exerted by the subject onto the support surfaces is transmitted to the sensing area. A data processor accepts the output signals from the force-sensing plate and calculates quantities related to the positions and magnitudes of forces exerted by the subject on the support surfaces. In order to permit biofeedback training, means for displaying position and magnitude quantities calculated by the computational means and for displaying additional quantities related to performance goals is provided so that the subject can see these quantities while performing the mobility task.

In a preferred embodiment of the invention, the support surfaces have markings indicating preferred positions where the subject should place a part of his or her body. The plurality of support surfaces, in one embodiment, includes a single surface parallel with the forceplate's top surface and a portion of the area of the forceplate's top surface, so as to form a single step or a seat. In another embodiment, the plurality of surfaces includes a staircase-like series of non-overlapping surfaces parallel with one another and the forceplate's top surface and at progressively greater distances above the forceplate's top surface.

A subject is placed in an initial position with one or more portions of his or her body in contact with at least one of the support surfaces, and then instructed to perform a movement protocol in which portions of the body in contact with support surfaces are lifted in accordance with the protocol and then placed at other locations on one of the support surfaces. By displaying on a continuous basis one or more of the calculated quantities related to the positions and magnitudes of forces exerted by the subject on the support surfaces, while also displaying one or more quantities related to a performance goal, the subject can train doing the mobility task using biofeedback.

The invention is intended for routine clinical use and therefore is designed to avoid the expense and complex operational demands imposed by optical motion analysis or the use of more than a single forceplate.

DESCRIPTION OF THE DRAWINGS

FIG. 11 illustrates a biofeedback display used in accordance with the frontal stair-climb training protocol shown in FIG. 10.

FIG. 12 illustrates a display of a performance goal in accordance with the frontal stair-climb training protocol shown in FIG. 10.

FIG. 13 illustrates a display of a performance goal in accordance with a lateral stair-climb training protocol.

DESCRIPTION OF SPECIFIC EMBODIMENTS

Embodiments of the present invention permit the assessment and biofeedback training of a subject's coordination, strength, and movement speed skills related to balance while performing balance and mobility tasks, such as stepping, stair climbing, sitting and rising from a chair. A structure, which in the preferred embodiments has a plurality of surfaces, allows the subject to perform the balance and mobility tasks. The subject's performance is measured and displayed in order to provide biofeedback information to the subject. In order to measure performance, quantities related to a subject's coordination, strength, and movement speed may be measured in real time. These quantities may be displayed relative to balance performance goals in order to provide helpful biofeedback information to the patient.

Figure 1:
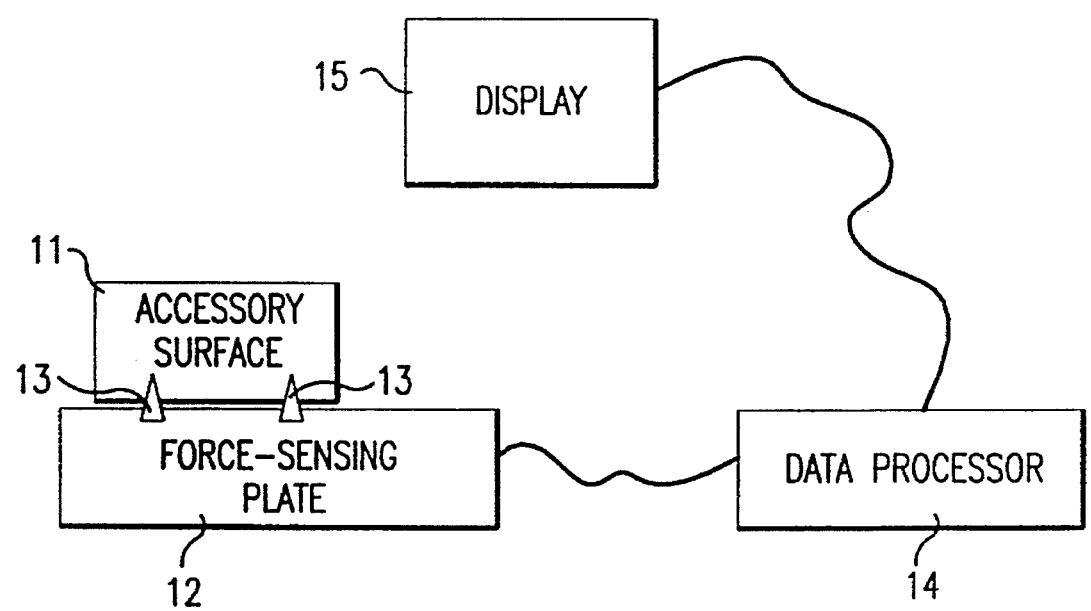
FIG. 1 shows the principal components of a preferred embodiment of the present invention.

FIG. 1 shows components that are common to all the preferred embodiments of the invention. As shown in FIG. 1, an accessory, consisting of one or more support surfaces 11, upon which the subject may stand, step or sit, is mounted on the top surface (the sensing area) of a force-sensing plate 12 (i.e., a forceplate). Positional restraints 13 fix the placement of the accessory surfaces relative to the force-sensing plate 12. Forces exerted on the accessory surfaces 11 are transmitted through to the force-sensing plate 12. Markings may be placed on the accessory surfaces 11 and the force-sensing plate 12, in order to indicate to the subject where to place his or her feet, and in some embodiments where to sit. (The embodiments discussed below have markings on both the accessory surfaces 11 and the force-sensing plates 12. The top surface of the force-sensing plate 12 can be one of the support surfaces 11 that the subject may stand or step on. It will be appreciated that accessory surfaces 11 can be made so that they completely cover the force-sensing plate 12 or be otherwise arranged so that the subject does not need to step directly on the force-sensing plate 12. Such an arrangement can be used in the same way as the embodiments described below; the lowest accessory surface may be considered analogous to the force-sensing plate.)

A data processor 14 receives signals representing the force information from the force-sensing plate 12 and, using computational methods described in the prior art, calculates on a continuous basis quantities related to the position and the magnitude of the force exerted against the force-sensing plate 12 by a subject standing with both feet supported by the force-sensing plate 12 and the accessory surfaces 11. A display means 15 displays the calculated quantities related to the position and magnitude of force, as well as additional quantities related to a performance goal.

Information regarding the positions of the accessory surfaces 11 relative to the force-sensing plate 12 and regarding the positions of markings on the force-sensing plate 12 and the accessory surfaces 11 input into the data processor 14, so that the data processor 14 can calculate on a continuous basis additional quantities related to the position of the center of force relative to markings on the force-sensing plate and accessory surfaces and the magnitude of force exerted by each leg.

A display 15 displays one or more quantities related to the forces exerted by those portions of a subject's body in contact with the force-sensing plate 12 and accessory surfaces. The display 15 may display an additional one or more quantities related to a performance goal.

A. Step-Up and Step-Down

Figure 2:
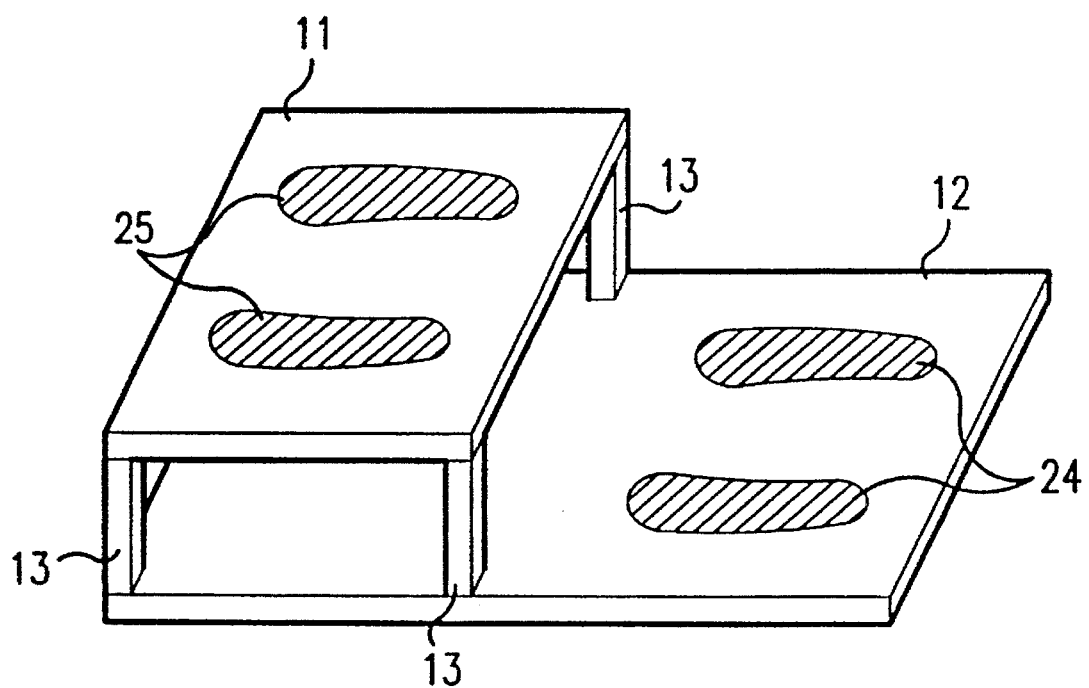
FIG. 2 illustrates a preferred embodiment of the invention used to assess and to train skills related to balance while stepping up and down between surfaces of two heights.

One preferred embodiment of the present invention is intended for assessment and biofeedback training of coordination skills related to balance while stepping up and stepping down between surfaces of two differing heights. As shown in FIG. 2, a removable accessory step surface 11 is mounted on a force-sensing plate 12. The positional restraints 13 mount into specified locations on the forceplate surface. Markings placed at defined positions on the forceplate 24 and accessory 25 surfaces indicate preferred placement positions for the feet.

Figure 3A:
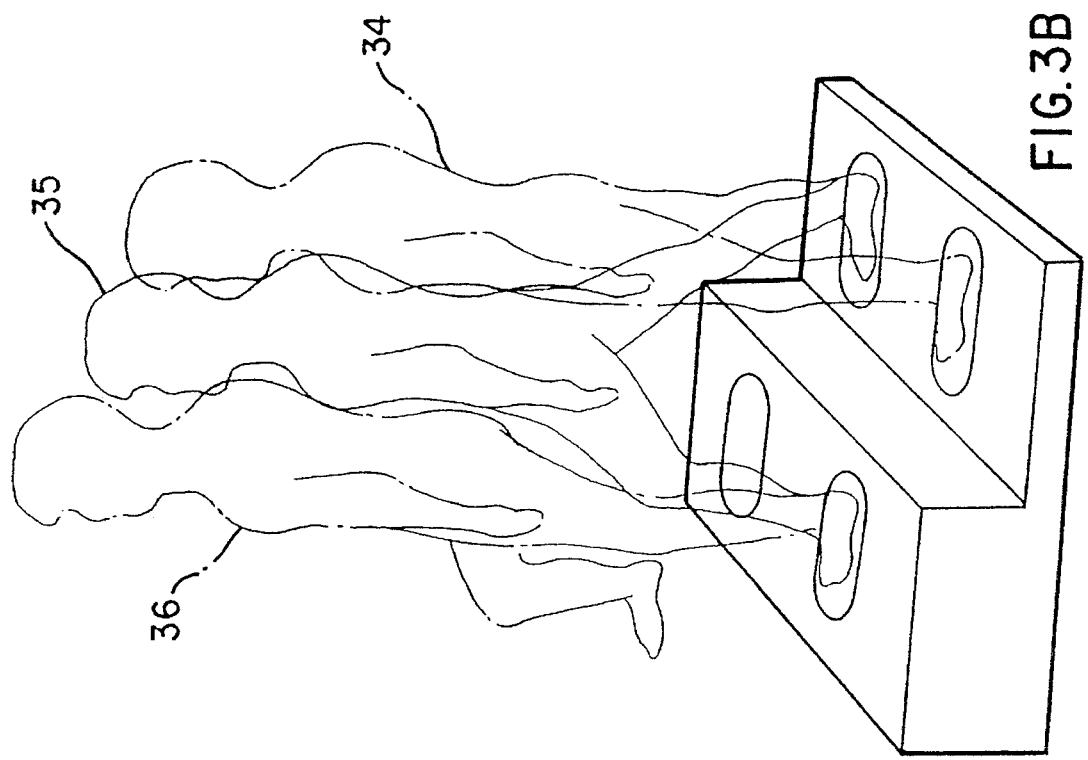
FIGS. 3A and 3B illustrates a frontal step-up training protocol in accordance with the embodiment depicted in FIG. 2.
Figure 3B:
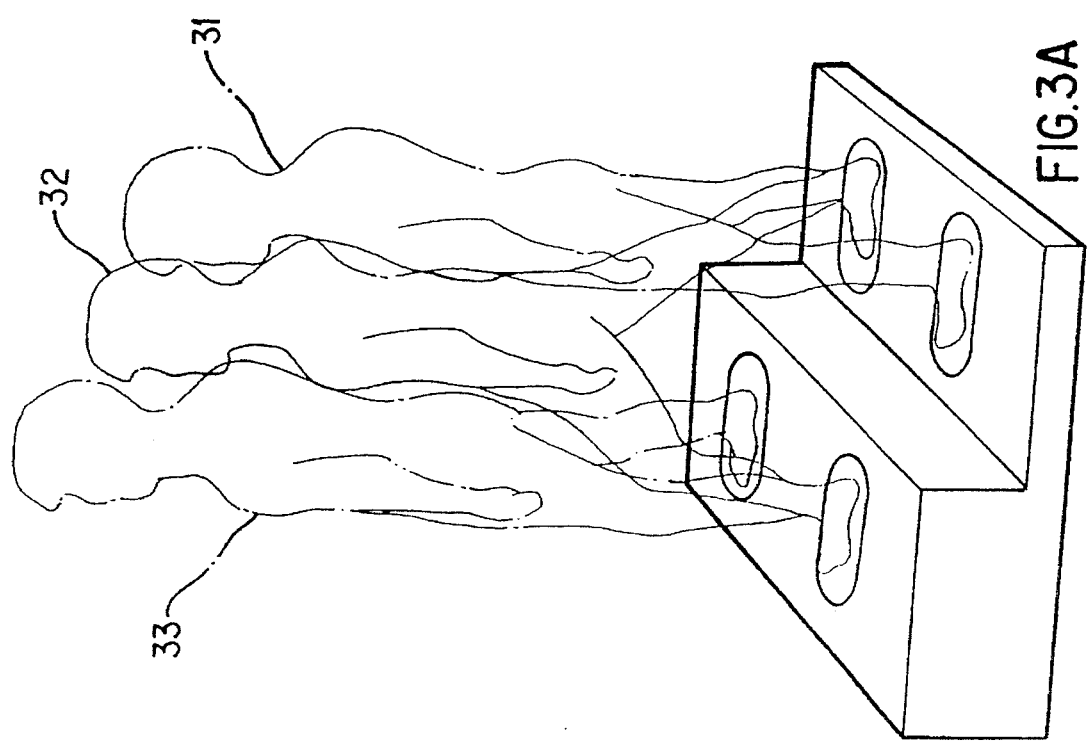

A frontal step-up training protocol in accordance with the FIG. 2 embodiment is illustrated in FIGS. 3A and 3B. The subject stands in the initial first position 31 with each of the two feet forward facing at preferred positions relative to markings on the forceplate support surface. The subject is in the second position 32 after the leg designated as leading (left) lifts from the forceplate support surface and is placed relative to markings on the accessory step surface. The subject is in the third position 33 after the following (right) leg lifts from the forceplate surface and is placed relative to markings on the accessory step surface. In an alternative version of the frontal step-up training protocol, the first 34 and second 35 positions are the same as above. The subject remains standing on the leading leg in the third position 36.

Figure 4:
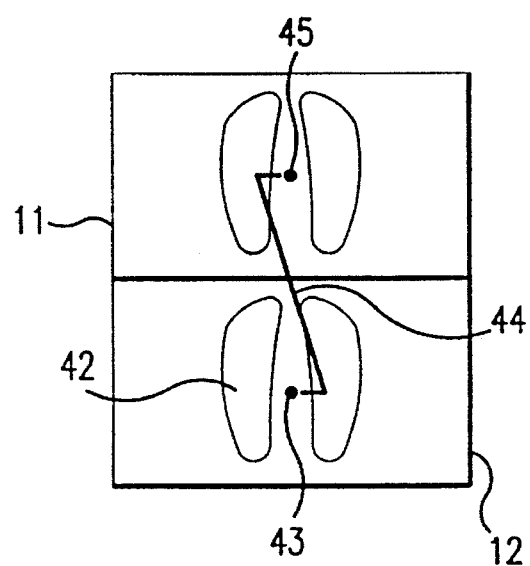
FIG. 4 illustrates a biofeedback display used in accordance with the frontal step-up training protocol shown in FIGS. 3A an 3B.

The display means illustrated in FIG. 4 displays a cursor quantity related to the position of the center of force relative positions on the forceplate surface. The positions of the forceplate 12 and accessory surfaces 11 and the positions of markings 42 are outlined on the display. Point 43 is the position of the cursor of a typical normal subject prior to initiation of the stepping up by the leading (left) leg. Z-shaped trace 44 is the cursor trajectory from the time the leading leg lifts from the forceplate surface until the following (right) leg is also placed on the accessory step surface. Point 45 is the cursor position after placement of the following leg on the step surface. If the alternative version of the step-up protocol shown in FIGS. 3A and 3B is followed, the trajectory would end with the cursor centered over the left foot mark, rather than returning to the center position.

Figure 5:
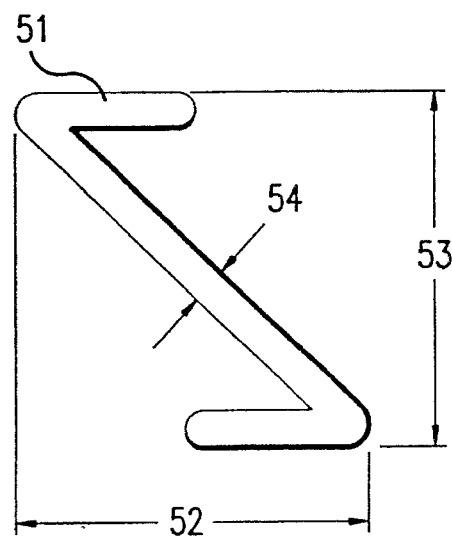
FIG. 5 illustrates a display of a performance goal in accordance with the frontal step-up training protocol shown in FIGS. 3A and 3B.

The display means shown in FIG. 5 displays a balance performance goal for the frontal step-up movement. A Z-shaped area 51 is based on the cursor trajectory of a typical normally coordinated and balanced frontal step-up movement. The dimensions of the preferred Z-shaped balance performance goal can be adjusted to train specific components of the subject's balance performance. For example, reducing the lateral dimension of the Z-shaped area 52 trains the subject to maintain balance while reducing the lateral spacing between the feet during step-ups. Increasing the Z-shaped area's longitudinal dimension 53, in contrast, trains the subject to increase the step length. Reducing the Z-shaped area's width 54 trains the subject to increase the precision of lateral balance during step-ups. If the alternative step-up protocol is used, the top horizontal segment of the Z-shaped area would be removed.

Figure 6C:
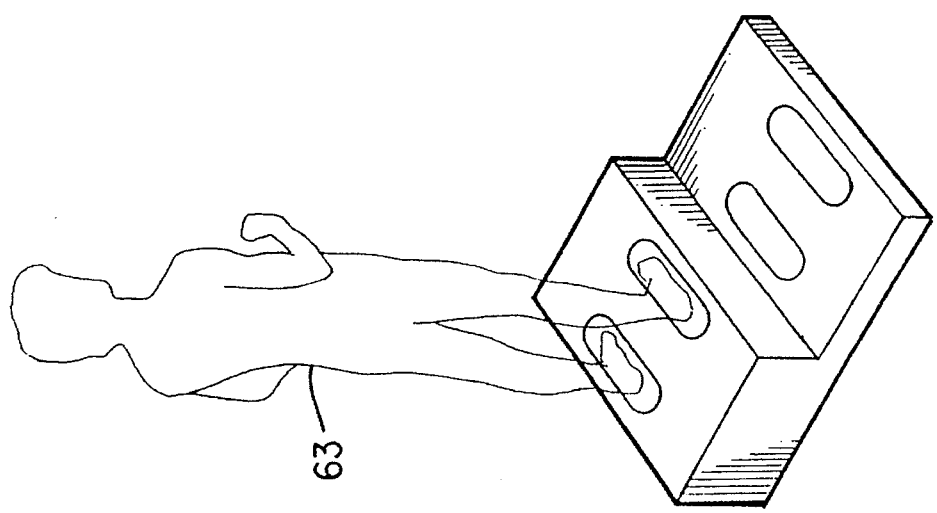
FIGS. 6A, 6B 6C and illustrates a lateral step-up training protocol used with the embodiment shown in FIG. 2.
Figure 6B:
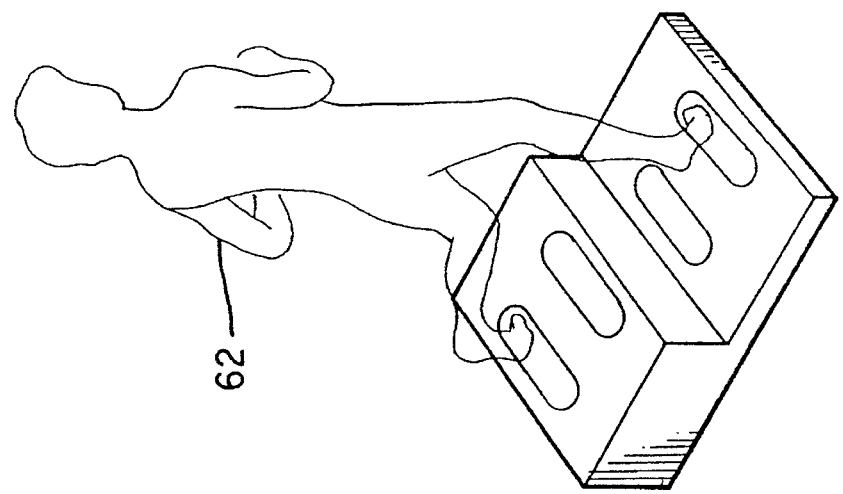
Figure 6A:
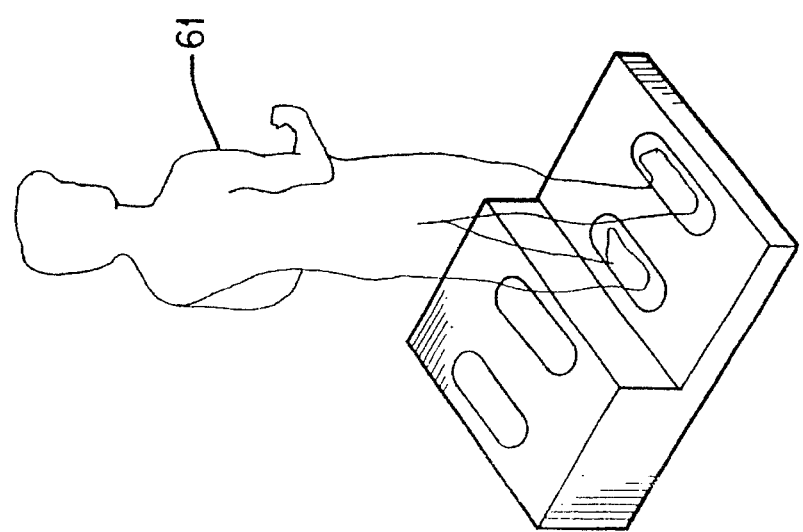

An alternative lateral step-up training protocol, which may be used with the FIG. 2 embodiment, is illustrated in FIGS. 6A, 6B and 6C. The subject stands in the initial first position 61 with each of the two feet laterally placed at preferred positions relative to markings on the forceplate surface. The subject is in the second position 62 after the leg designated as leading (left) lifts from the forceplate surface and is placed relative to markings on the accessory step surface. The subject is in the third position 63 after the following leg (right) lifts from the forceplate surface and is placed at a second position relative to markings on the accessory step surface. By facing the subject in the opposite lateral direction, it is possible to designate the right leg as leading and the left as following.

Figure 7:
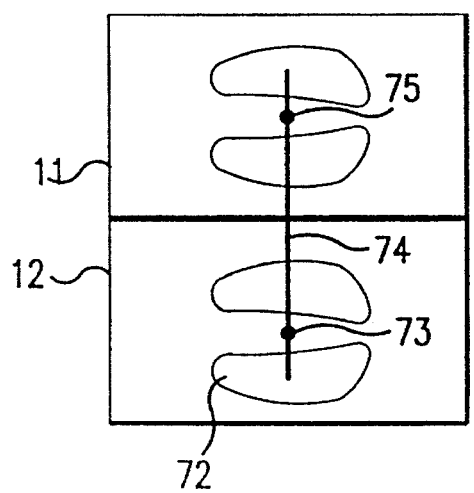
FIG. 7 illustrates a biofeedback display used in accordance with the lateral step-up training protocol shown in FIG. 6A, 6B and 6C.

The display means shown in FIG. 7 displays the cursor trajectory produced by a typical normal subject during the lateral step-up movement. The forceplate 12 and accessory surface areas 11 and markings 72 are outlined on the display. Point 73 is the position of the cursor prior to initiation of the lateral step-up. Line 74 is the cursor trajectory from the time the leading leg lifts from the forceplate surface until it is placed on the accessory step surface. Point 75 is the cursor position after the following leg steps up to the accessory step surface.

Figure 8:
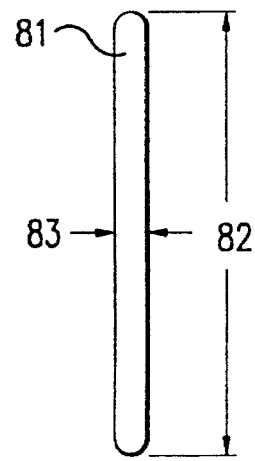
FIG. 8 illustrates a display of a performance goal in accordance with the lateral step-up training protocol shown in FIG. 6.

The display means shown in FIG. 8 displays a performance goal for the lateral step-up movement, an I-shaped area 81 based on the center of force trajectory produced by a typical normally coordinated and balanced lateral step-up movement. The dimensions of the preferred I-shaped area can be adjusted to train specific components of the subject's performance. For example, increasing the I-shaped area's longitudinal dimension 82 trains the subject to increase the lateral step width, while reducing the I-shaped area's width 83 trains the subject to increase the precision of forward-backward balance during steps.

By reversing the sequences of events followed during the frontal and lateral step-up movements shown in FIGS. 3A, 3B and 6A–6C, respectively, the assessment and biofeedback training can be provided for coordination and balance skills during frontal and lateral step-down movements in accordance with the FIG. 2 embodiment. For step-down movements, biofeedback cursors, performance goal areas, and preferred foot positions are similar to those used with step-up movements. To train step-down balance skills, the subject begins the protocol at preferred positions on the accessory surface 11 and then steps down to preferred positions on the forceplate surface 12.

It is further possible to orient the accessory step surface in positions other than parallel with the forceplate surface. Accessory surfaces tilted with respect to the forceplate surface provide the subject with an additional challenge to the balance system. Therefore, accessory surface tilting is another variable that can be used to increase or decrease the difficulty of the training task. The methods for marking locations on the forceplate and accessory surfaces, measuring quantities related to the forces exerted by the subject's feet, and displaying these quantities relative to performance goals would be similar in the case of parallel and tilted accessory step surfaces.

B. Stair-Climb and -Descent Movements

Figure 9:
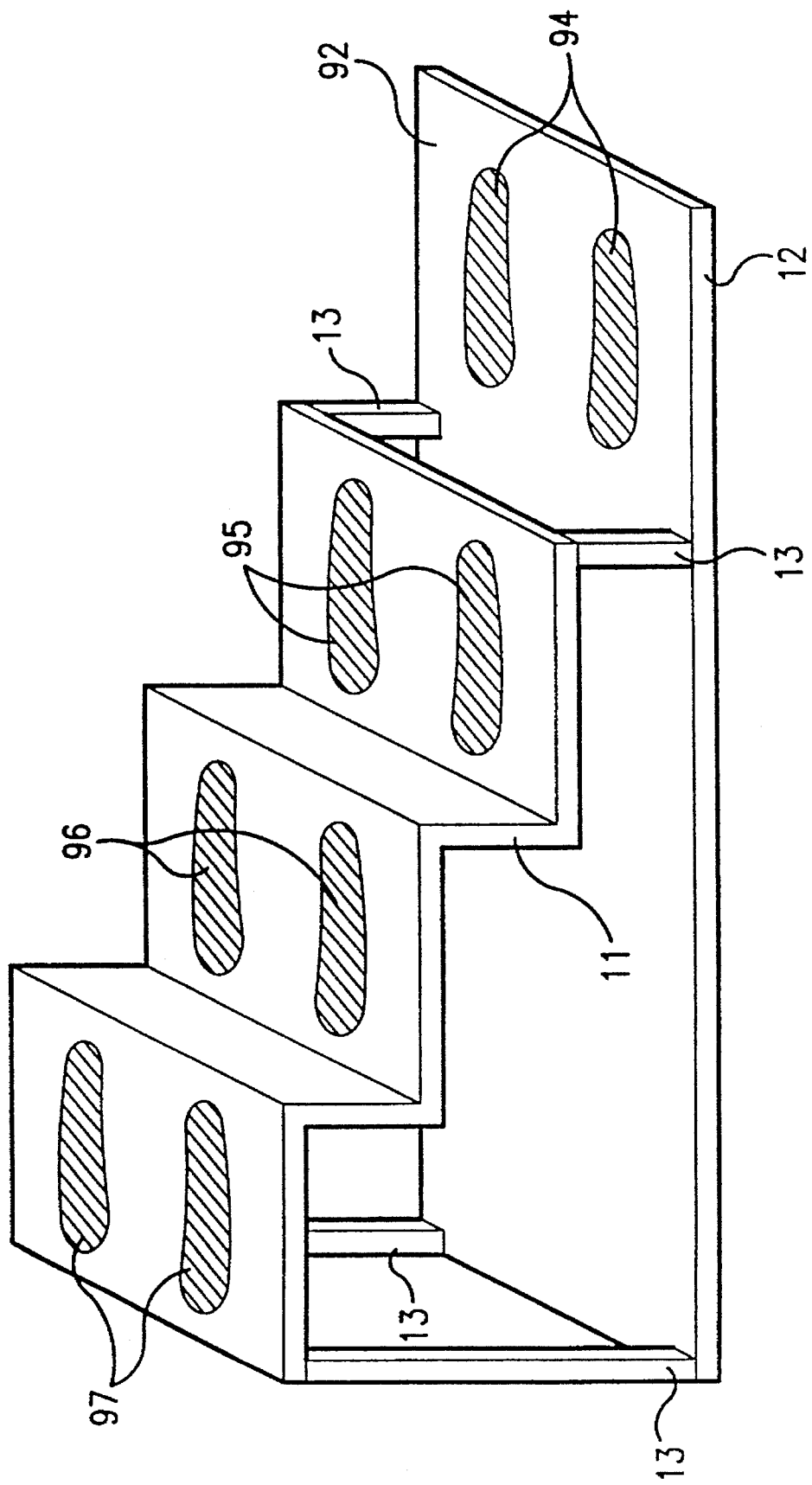
FIG. 9 illustrates another embodiment of the invention, using a removable accessory staircase.

Another embodiment of the present invention is illustrated in FIG. 9 is intended for assessment and training of coordination skills related to balance during the ascent and descent of stairs. A removable accessory staircase comprised of three levels is mounted on a forceplate surface 12. Positional restraints 13 at the four corners of the accessory staircase surface mount at specified locations on the forceplate surface and thereby fix the location of the accessory surfaces relative to the forceplate surface. Markings on the forceplate 94 and stair levels one 95, two and three 97 indicate preferred placement positions for the feet when a subject performs stair-climbing and -descending movements. Other preferred embodiments may include accessory staircases with fewer or greater numbers of stair levels, the minimum being two and the maximum restrained only by practical limits of device size and weight.

Figure 10:
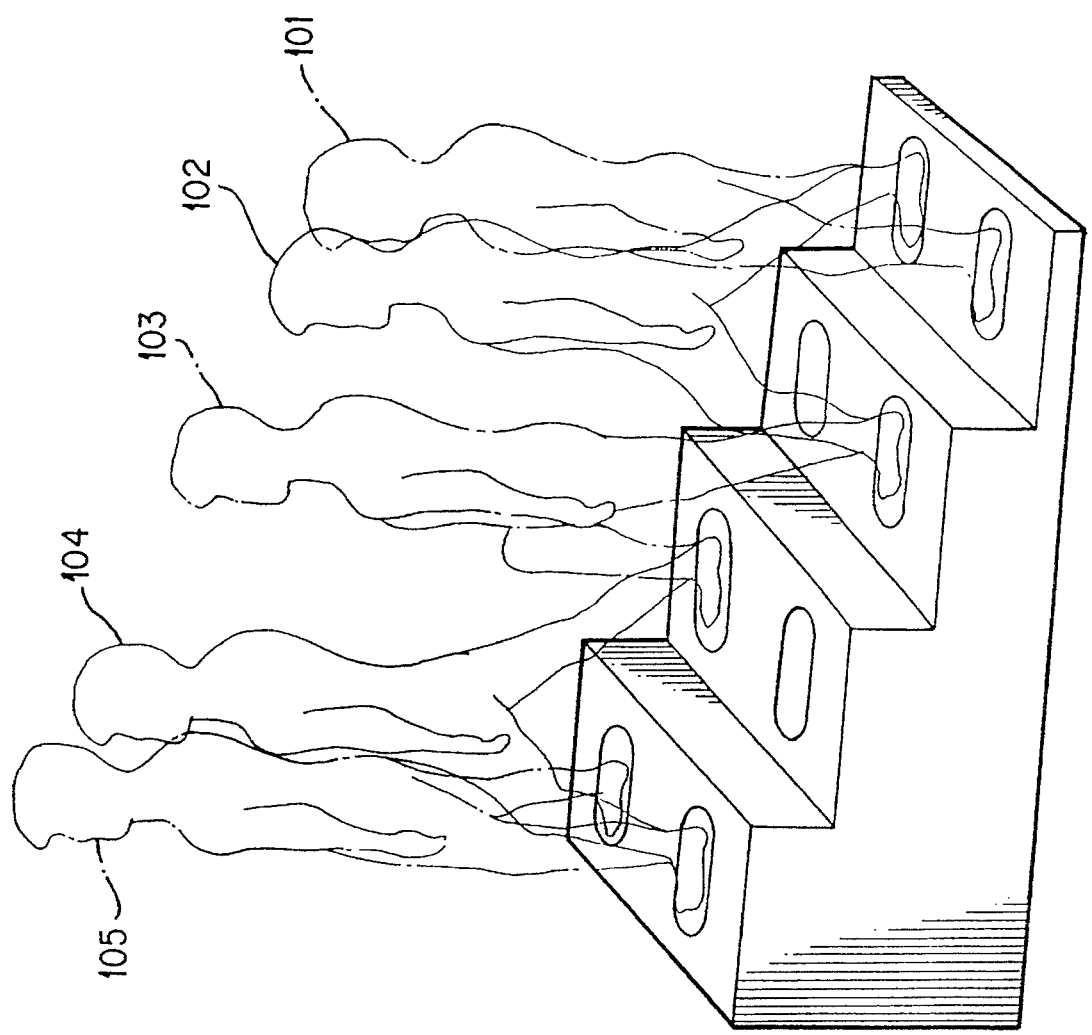
FIG. 10 illustrates a frontal stair-climb training protocol in accordance with the embodiment shown in FIG. 9.

A frontal stair-climb training protocol for use with the FIG. 9 embodiment is illustrated in FIG. 10. The subject stands in the initial first position 101 with the two feet placed frontally at preferred positions relative to markings on the forceplate surface. The subject is in the second position 102 after the leg designated as leading (left) lifts from the forceplate support surface and is placed on the first staircase level. The subject is in the third position 103 after the following leg (right) lifts from the forceplate support surface and is placed on the second staircase level. The subject is in the fourth position 104 after the leading leg lifts from the first staircase level and is placed on the third staircase level. The subject is in the fifth and final position 105 after the following leg lifts from the second and is placed on the third staircase level.

The display means illustrated in FIG. 11 displays as a moving cursor a quantity related to the continuously calculated position of the center of force on the forceplate surface. The positions of the forceplate 12 and the accessory step surfaces 11 and the markings 112 are outlined on the display. Point 113 shows the position of the cursor of a typical normal subject in the first position prior to stair-climb initiation. Line 114 shows the cursor trajectory from the time the leading leg lifts from the forceplate surface until it is placed on the surface of the first staircase level. Line 115 shows the cursor trajectory from the time the following leg lifts from the forceplate surface until it is placed on the surface of the second staircase level. Line 116 shows the cursor trajectory from the time the leading leg lifts from the surface of the first staircase level until it is placed on the surface of the third staircase level. Point 117 shows the position of the cursor following completion of the stair climb.

The display means illustrated in FIG. 12 displays a preferred performance goal for the frontal stair-climb movement. A zigzag-shaped area 121 is based on the center of force trajectory produced by a typical normally coordinated and balanced frontal stair climb. The dimensions of the preferred zigzag-shaped performance goal can be adjusted to train specific components of the subject's stair-climbing performance. For example, reducing the zigzag-shaped area's lateral dimension 122 trains the subject to maintain balance while narrowing the lateral spacing between the feet during stair climbs. Increasing the longitudinal dimensions of individual segments of the zigzag-shaped area 123, in contrast, trains the subject to increase the length of steps. Finally, reducing the zigzag-shaped area width 124 trains the subject to increase the precision of lateral balance during stair climbs.

A lateral stair-climb protocol may be performed in accordance with devices and methods of the FIG. 9 embodiment. Initially, the subject stands with each of the two feet laterally placed at preferred positions relative to markings on the forceplate surface. During the first phase of movement the leg designated as leading (closest to the step) lifts from the forceplate surface and is placed on the first stair level. During the second phase of movement the following leg lifts from the forceplate surface and is placed on the first stair level. The sequence of leading and following leg lifts and placements is repeated to climb from the first to the second and then from the second to the third stair levels. By reversing the lateral direction of the subject's orientation, it is possible to designate either the left or right leg as leading.

When a lateral stair-climb movement is performed by a normal subject, the cursor follows a linear trajectory similar to that produced by a single lateral step-up movement. Rather than moving the entire distance in one phase, however, the trajectory is divided into segments, each segment corresponding to one stair level. A preferred performance goal for the three-level lateral stair climb, therefore, is the three-segment I-shaped area shown by the display means illustrated in FIG. 13.

By reversing the sequences of the stair-climb events described above, the resulting protocol assesses and provides biofeedback training during frontal and lateral staircase descents. For descent movements, biofeedback cursors, performance goal areas, and preferred foot positions are similar to those used for the training of stair-climb movements. Now, the subject is initially positioned on the third level in the initial phase and steps down in sequence to the second, first, and then the forceplate level.

It is further possible to orient the accessory stair level surfaces in positions other than parallel with the forceplate surface. Accessory stair surfaces tilted with respect to the forceplate surface provide the subject with an additional challenge to the balance system. Therefore, surface tilting is another variable that can be used to increase or decrease the difficulty of the training task. The methods for marking locations on the forceplate and accessory stair surfaces, measuring quantities related to the forces exerted by the subject's feet, and displaying these quantities relative to performance goals would be similar in the case of parallel and tilted accessory stair surfaces.

C. Sitting and Rising From a Chair

Figure 14:
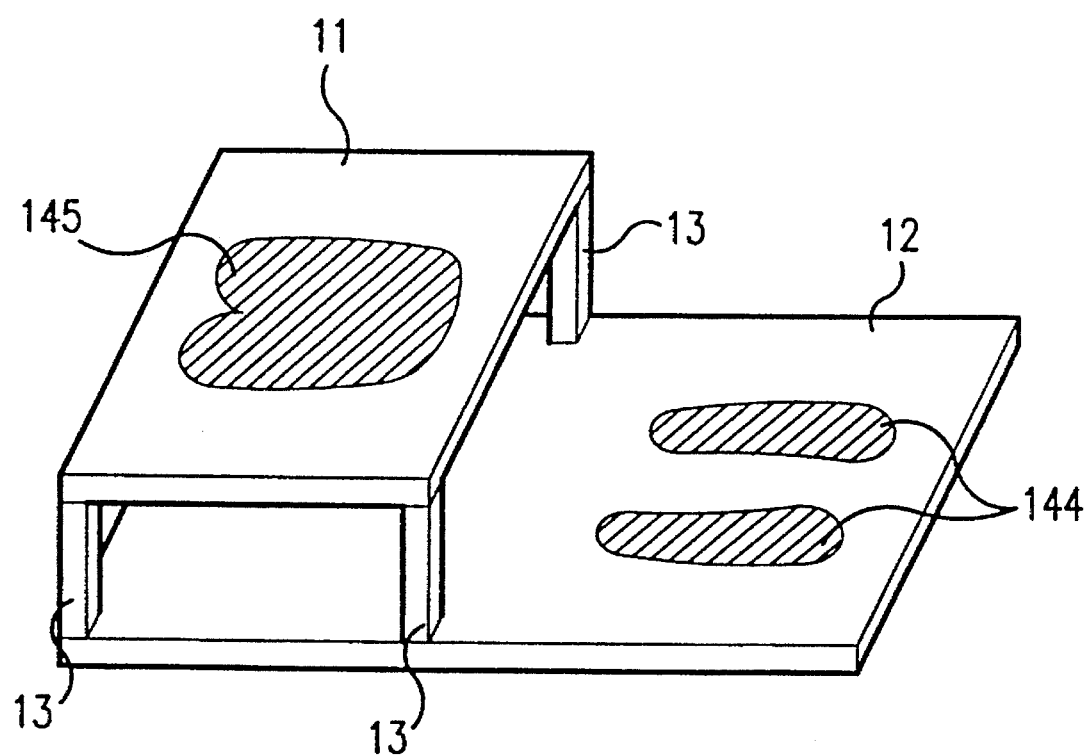
FIG. 14 illustrates further embodiment of the invention, using a removable accessory seat surface.

The embodiment of the present invention illustrated in FIG. 14 is intended for assessment and training of coordination skills related to balance during sitting down and rising from a seated surface. A removable accessory seat surface 11 is mounted on a forceplate support surface 12 with positional restraints 13. Markings placed at defined positions on the forceplate 144 and seat 145 surfaces indicate preferred placement positions for the feet and buttocks, respectively, when a subject performs a sitting or rising movement.

Figure 15:
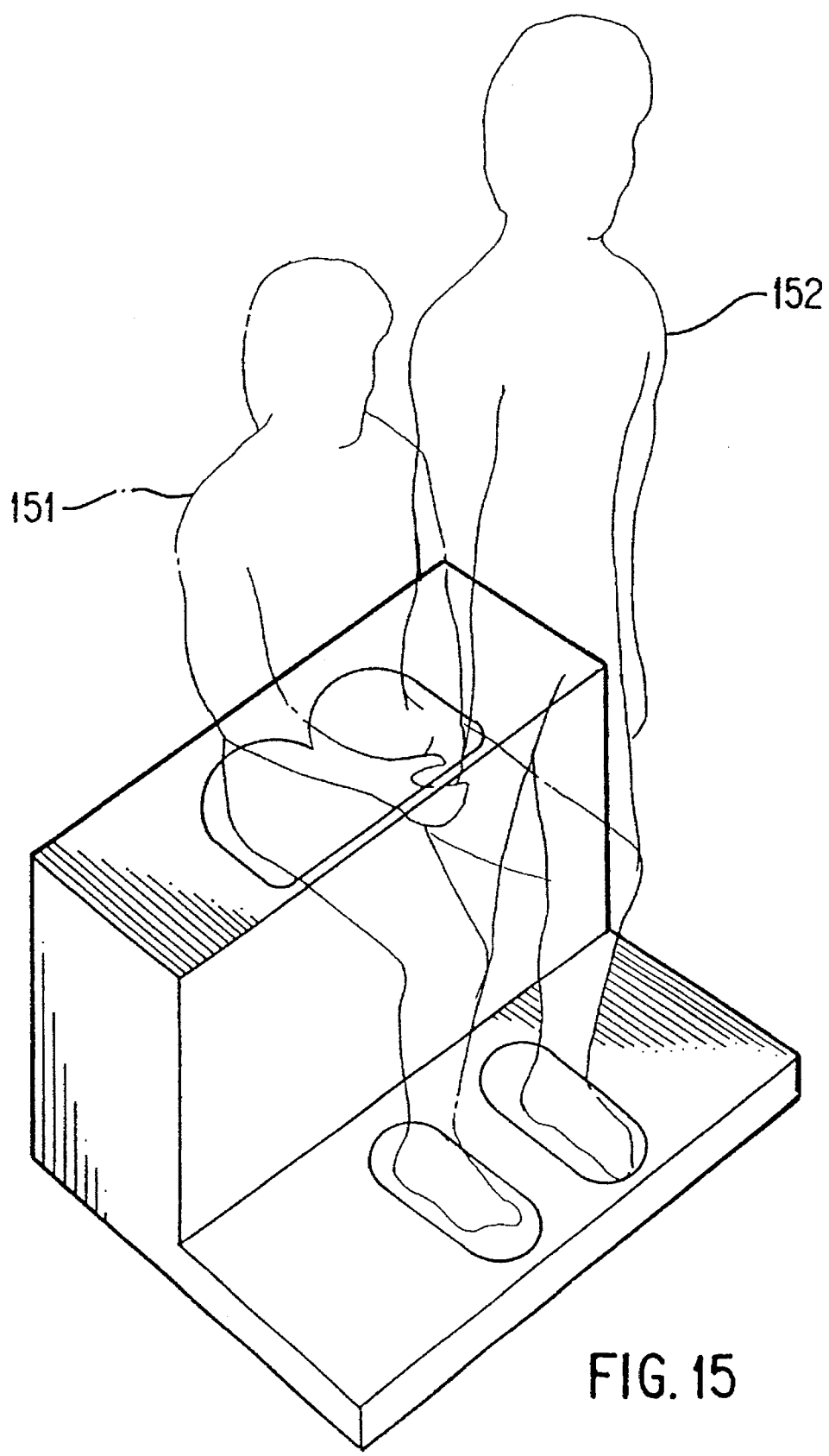
FIG. 15 illustrates training protocol for rising from a seated position in accordance used with the embodiment shown in FIG. 14.

The training protocol for rising from a seated surface in accordance with the FIG. 14 embodiment is illustrated in FIG. 15. The subject in the initial first position 151 is seated with the buttocks and feet placed at preferred positions relative to markings on the seat and forceplate surfaces. The subject is in the second position 152 after performing the rising movement.

Figure 16:
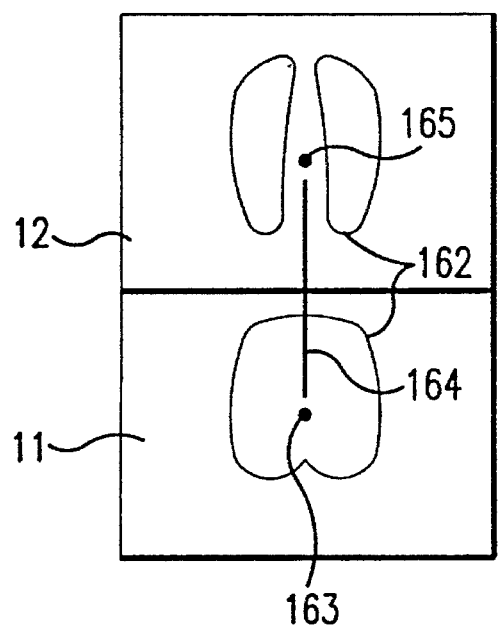
FIG. 16 illustrates a biofeedback display used with the training protocol shown in FIG. 15.

The display means illustrated in FIG. 16 displays a moving cursor quantity related to the continuously calculated position of the center of force on the forceplate surface. The positions of the forceplate 2 and accessory seat surfaces 11 and the markings 162 are outlined on the display. Point 163 is the cursor position of a typical normal subject prior to rising from the seat surface. Trace 164 is the cursor trajectory from the time the rising movement begins until the subject reaches an erect standing position. Point 165 is the cursor position following completion of the rising movement.

Figure 17:
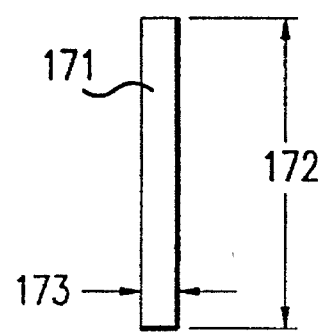
FIG. 17 illustrates a display of a performance goal in accordance with the training protocol shown in FIG. 15.

The display means illustrated in FIG. 17 displays a preferred performance goal for the rising movement. Area 171 is an I-shaped performance goal based on the center of force trajectory produced by a typical normally coordinated and balanced rising movement. The dimensions of the preferred I-shaped area can be adjusted to train specific components of the subject's rising-from-a-chair performance. For example, increasing the I-shaped area longitudinal dimension 172 trains the subject to rise when the feet are placed further forward relative to the buttocks, while reducing the I-shaped area's width 173 trains the subject to increase the precision of lateral balance during rising movements.

By reversing the sequence of the rising events illustrated in FIG. 15, the resulting protocol assesses and provides biofeedback training of sitting movements in accordance with the FIG. 14 embodiment. For sitting movements, biofeedback cursors, performance goal areas, and foot and buttocks positions are similar to those used with rising movements. For the alternative sitting protocol, the subject is initially positioned in an erect standing position on the forceplate surface and then sits down onto the seat surface.

D. Strength and Speed

The specific embodiments set forth above describe devices and methods for assessment and biofeedback training of coordination skills related to balance. Additional display methods may be used with these devices and methods may be used to assess and train the strength and speed of the subject in performing the various protocols set forth above. Specifically, the additional display methods described hereinbelow are intended for use with the step, stair-climb, and seat accessories (FIGS. 2, 9 and 14, respectively) and the movement protocols associated with each of these accessories (FIGS. 3A and 3B, 10 and 15 respectively).

Figure 18:
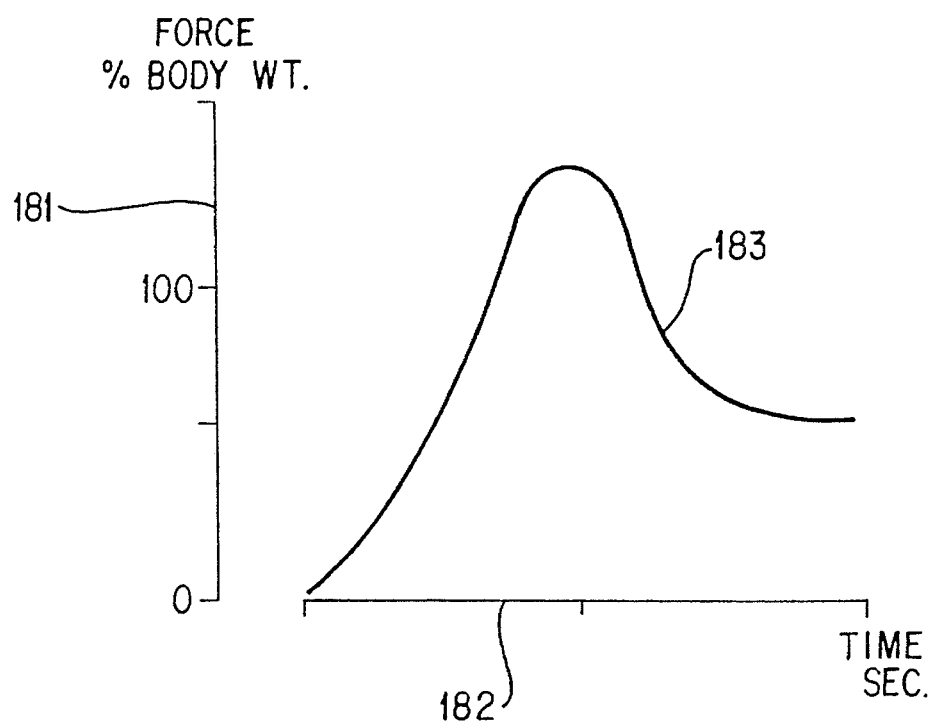
FIG. 18 illustrates a biofeedback display of quantities related to the strength and speed of movement of the leading leg during the frontal step-up training protocol.

The display means shown in FIG. 18 displays quantities related to the strength and speed of the force effort exerted by a leg of the subject as a function of time. The vertical axis 181 displays quantities related to the force exerted by a single leg, while the horizontal axis 182 displays the time over which the force is exerted. In a preferred embodiment of the display means, the vertical axis displays force as a percentage of the subject's total body weight and the horizontal axis displays time in seconds.

The display means shown in FIG. 18 displays the trajectory of a quantity related to the magnitude of force carried by the leading leg 183 during the step-up training protocol illustrated in FIGS. 3A and 3B. At time zero, the instant of leading leg contact with the accessory step surface, the leading leg force begins as zero percent of body weight. As the leading leg accelerates the body upward and forward onto the accessory step surface, and leading leg force increases to greater than 100 percent of body weight and then decreases to 50 percent of body weight as the following leg contacts the accessory step surface and assumes one-half the body weight.

If the alternative step-up protocol is used in which the subject maintains full body weight on the leading leg and the following leg is not brought into contact with the accessory step surface, the force exerted by the leading leg will decrease to 100 percent rather than 50 percent of body weight.

Figure 19:
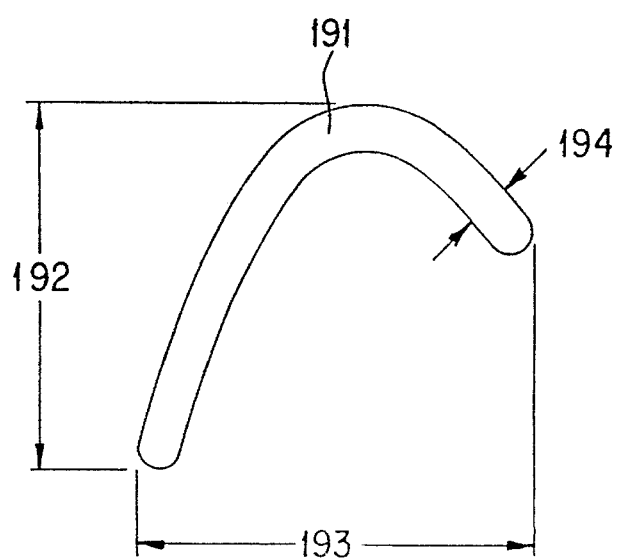
FIG. 19 illustrates a display of a movement strength and speed performance goal in accordance with the frontal step-up training protocol.

The display means shown in FIG. 19 displays a preferred arc-shaped strength and speed performance goal 191 based on the performance of the typical normal subject. The dimensions of the preferred arc-shaped performance goal area can be adjusted to train specific components of the subject's step-up performance. For example, increasing the height dimension of the arc 192 trains the subject to increase the magnitude of the leading leg upward force. Reducing the lateral dimension of the arc 193 trains the subject to increase the speed (reduce total time) of the step-up movement, while increasing the "roundness" of the arc area trains a smoother application of leg force. Decreasing the width 194 of the performance goal area makes the goal more difficult to attain.

Figure 20A:
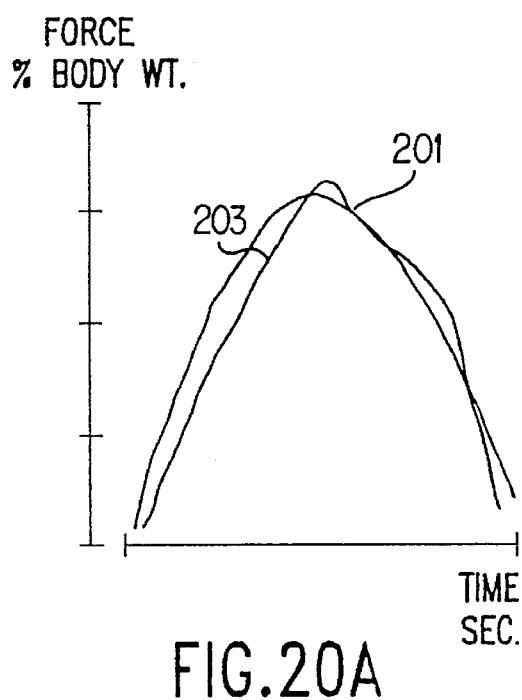
FIGS. 20A and 20B illustrate a biofeedback display of two consecutive force trajectories produced by the leading leg and then by the following leg during the stair-climb training protocol.
Figure 20B:
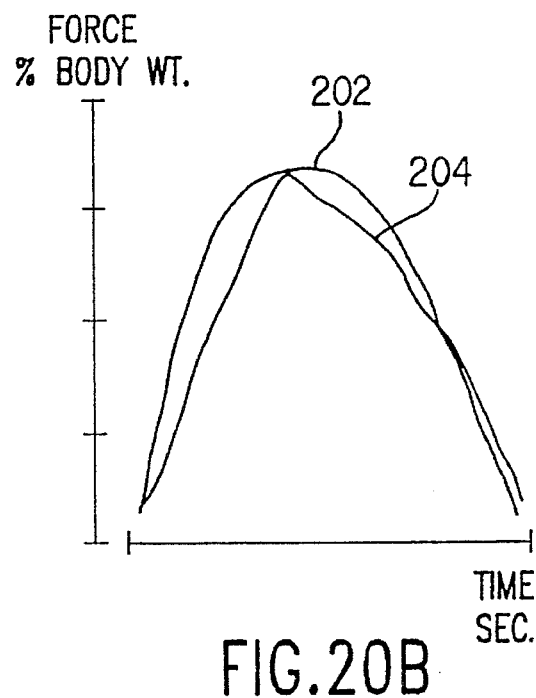

The display means shown in FIG. 20 displays the trajectories of quantities related to the magnitudes of force carried by the leading 201 and following 202 legs as functions of time for alternate step-ups during the stair-climb protocol illustrated in FIG. 10. When the preferred embodiment with three staircase levels is used, the leading leg 203 and the following leg 204 each produce a second overlying step-up force trajectory. In other preferred embodiments, the number of overlapping force trajectories for each leg may be one or greater than two, depending on the number of stair-climb levels.

Figure 21:
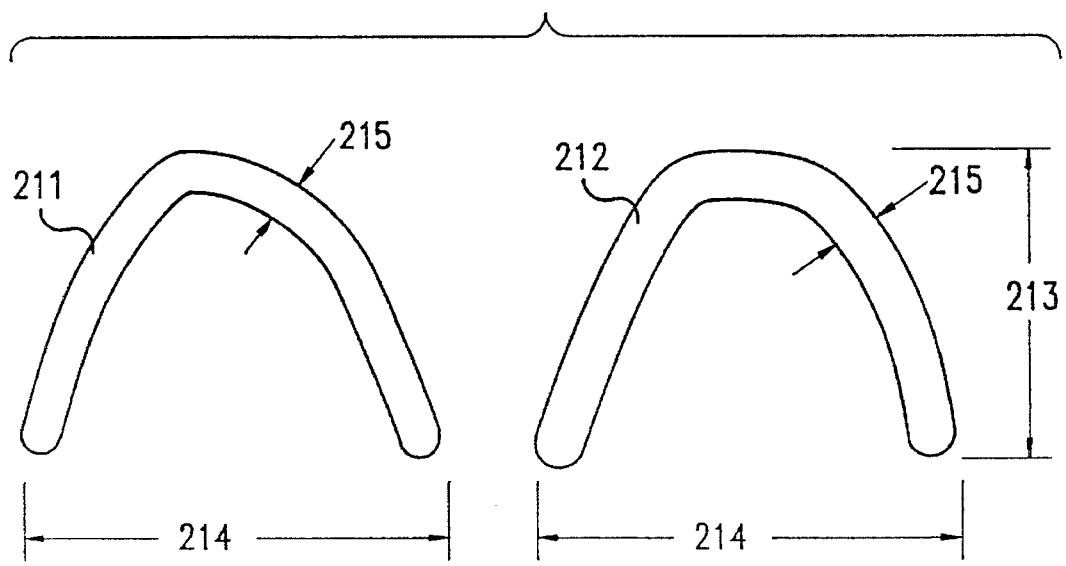
FIG. 21 illustrates a display of movement strength and speed performance goals for the leading and following legs in accordance with the stair-climb training protocol.

The display means shown in FIG. 21 displays preferred strength and speed performance goals for the left and right legs during the stair-climb training protocol. Arc-shaped areas 211 and 212 are based on the desired alternate force trajectories produced by the leading and following legs of the typical normal subject. By adjusting the height 213, lateral dimension 214, area width 215 and roundness of the performance goal areas of FIG. 21, it is possible to train subjects to modify the level, speed, repeatability, and smoothness of the leading and following leg force efforts in ways similar to those described for the leading leg for the step-up protocol.

Display means similar to that shown in FIG. 20 can be used to display trajectories of quantities related to the forces exerted by each of the two legs of a typical normal subject during the sit-to-stand protocol illustrated in FIG. 15. Instead of alternating, the forces of the two leg are exerted simultaneously. Furthermore, instead of forces exceeding 100 percent of body weight during the upward thrusting phase of movement, forces exerted by each leg would exceed 50 percent of body weight during the upward thrust and then decrease to 50 percent following completion of the movement.

Performance goal display means similar to those shown in FIG. 20 can be used to display performance goals related to the forces exerted by each of the two legs during the sit-to-stand protocol. Arc-shaped performance goal areas can be based on the trajectories produced by a typical normal subject during sit-to-stand movements. Therefore each leg would begin at zero force, increase to a level greater than 50 percent of body weight, and then decrease to 50 percent of body weight.

In other preferred embodiments using similar biofeedback displays of quantities related to leg force and time, it is also possible to train strength and speed skill during step-down, staircase-descent, and sitting protocols.

What is claimed is:

1. An apparatus for assessing and biofeedback training of movement coordination, strength, and speed skills critical to balance during a mobility task performed by a subject moving from a first position to a second position on a combination of surfaces, the apparatus comprising:

force-sensing means, having a sensing area, for measuring the forces exerted on the sensing area and transmitting output signals representative of the measured forces, the forces having a center of force on the sensing area;

a plurality of support surfaces mounted in specified positions relative to the sensing area and such that substantially all forces exerted by the subject onto the support surfaces is transmitted to the sensing area, wherein the support surfaces and the sensing area are arranged so as to support the subject's entire weight while the subject is in the first position, while the subject is in the second position and while the subject is performing the mobility task moving from the first position to the second position, each support surface having a non-overlapped area at least large enough to accommodate a foot of the subject;

computational means for accepting the output signals from the force-sensing means and calculating the center of force exerted by the subject on the support surfaces; and display means for displaying the movement of the center of force calculated by the computational means and for displaying as a performance goal a trajectory of the center of force representative of a normally coordinated and balanced subject performing the mobility task moving from the first position to the second position.

2. An apparatus according to claim 1, wherein the support surfaces have markings indicating preferred positions where the subject should place a part of the subject's body while in the first position and while in the second position.

3. An apparatus according to claim 1, wherein the force-sensing means includes a forceplate, wherein the forceplate has a top surface;

wherein one of the support surfaces is a first surface which is parallel to and spaced away from the forceplate's top surface and which is smaller than the sensing area of the force-sensing means so that a portion of the forceplate's top surface is not overlapped by the first surface; and wherein a second support surface is the portion of the forceplate's top surface not overlapped by the first surface.

4. An apparatus according to claim 1, wherein the force-sensing means is a forceplate and the plurality of support surfaces includes a staircase-like series of non-overlapping surfaces parallel with one another and the forceplate's top surface and at progressively greater distances above the forceplate's top surface.

5. An apparatus according to claim 1, wherein the support surfaces are arranged so that the subject may be in contact with a different support surface in the second position from the support surface in contact with the subject in the first position.

6. An apparatus according to claim 5, wherein the support surfaces have markings indicating preferred positions where the subject should place a part of the subject's body while in the first position and while in the second position.

7. An apparatus according to claim 5, wherein the force-sensing means includes a forceplate, wherein the forceplate has a top surface;

wherein one of the support surfaces is a first surface which is parallel to and spaced away from the forceplate's top surface and which is smaller than the sensing area of the force-sensing means so that a portion of the forceplate's top surface is not overlapped by the first surface; and wherein a second support surface is the portion of the forceplate's top surface not overlapped by the first surface.

8. An apparatus according to claim 5, wherein the force-sensing means is a forceplate and the plurality of support surfaces includes a staircase-like series of non-overlapping surfaces parallel with one another and the forceplate's top surface and at progressively greater distances above the forceplate's top surface.

9. An apparatus according to claim 1, wherein the support surfaces are arranged so that the subject may be in contact with different areas of the support surfaces in the second position from the areas of the support surfaces in contact with the subject in the first position.

10. An apparatus according to claim 9, wherein the support surfaces have markings indicating preferred positions where the subject should place a part of the subject's body while in the first position and while in the second position.

11. An apparatus according to claim 9, wherein the force-sensing means includes a forceplate, wherein the forceplate has a top surface;

wherein one of the support surfaces is a first surface which is parallel to and spaced away from the forceplate's top surface and which is smaller than the sensing area of the force-sensing means so that a portion of the forceplate's top surface is not overlapped by the first surface; and wherein a second support surface is the portion of the forceplate's top surface not overlapped by the first surface.

12. An apparatus according to claim 9, wherein the force-sensing means is a forceplate and the plurality of support surfaces includes a staircase-like series of non-overlapping surfaces parallel with one another and the forceplate's top surface and at progressively greater distances above the forceplate's top surface.

13. An apparatus for assessing movement coordination, strength, and speed skills critical to balance during a mobility task performed by a subject moving from a first position to a second position on a combination of surfaces, the apparatus comprising:

force-sensing means, having a sensing area, for measuring the forces exerted on the sensing area and transmitting output signals representative of the measured forces, the forces having a center of force and a total magnitude on the sensing area;

a plurality of support surfaces mounted in specified positions relative to the sensing area and such that substantially all forces exerted by the subject onto the support surfaces is transmitted to the sensing area, wherein the support surfaces and the sensing area are arranged so as to support the subject's entire weight while the subject is in the first position, while the subject is in the second position and while the subject is performing the mobility task moving from the first position to the second position, each support surface having a non-overlapped area at least large enough to accommodate a foot of the subject; and computational means for accepting the output signals from the force-sensing means and calculating the center of force and the total magnitude of the forces exerted by the subject on the support surfaces; and display means for displaying the center of force and the total magnitude calculated by the computational means and for displaying a performance goal representative of a normally coordinated and balanced subject performing the mobility task moving from the first position to the second position.

14. An apparatus according to claim 13, wherein the support surfaces are arranged so that the subject may be in contact with a different support surface in the second position from the support surface in contact with the subject in the first position.

15. An apparatus according to claim 14, wherein the support surfaces have markings indicating preferred positions where the subject should place a part of the subject's body while in the first position and while in the second position.

16. An apparatus according to claim 14, wherein the force-sensing means includes a forceplate, wherein the forceplate has a top surface;

wherein one of the support surfaces is a first surface which is parallel to and spaced away from the forceplate's top surface and which is smaller than the sensing area of the force-sensing means so that a portion of the forceplate's top surface is not overlapped by the first surface; and wherein a second support surface is the portion of the forceplate's top surface not overlapped by the first surface.

17. An apparatus according to claim 14 wherein the force-sensing means is a forceplate and the plurality of support surfaces includes a staircase-like series of non-overlapping surfaces parallel with one another and the forceplate's top surface and at progressively greater distances above the forceplate's top surface.

18. An apparatus according to claim 13, wherein the support surfaces are arranged so that the subject may be in contact with different areas of the support surfaces in the second position from the areas of the support surface in contact with the subject in the first position.

19. An apparatus according to claim 18, wherein the support surfaces have markings indicating preferred positions where the subject should place a part of the subject's body while in the first position and while in the second position.

20. An apparatus according to claim 18, wherein the force-sensing means includes a forceplate, wherein the forceplate has a top surface;

wherein one of the support surfaces is a first surface which is parallel to and spaced away from the forceplate's top surface and which is smaller than the sensing area of the force-sensing means so that a portion of the forceplate's top surface is not overlapped by the first surface; and wherein a second support surface is the portion of the forceplate's top surface not overlapped by the first surface.

21. An apparatus according to claim 18, wherein the force-sensing means is a forceplate and the plurality of support surfaces includes a staircase-like series of non-overlapping surfaces parallel with one another and the forceplate's top surface and at progressively greater distances above the forceplate's top surface.

22. An apparatus for assessing and biofeedback training of movement coordination, strength, and speed skills critical to balance during a mobility task performed by a subject moving from a first position to a second position on a combination of surfaces, the apparatus comprising:

force-sensing means, having a sensing area, for measuring the forces exerted on the sensing area and transmitting output signals representative of the measured forces, the forces having a total magnitude on the sensing area;

a plurality of support surfaces mounted in specified positions relative to the sensing area and such that substantially all forces exerted by the subject onto the support surfaces is transmitted to the sensing area, wherein the support surfaces and the sensing area are arranged so as to support the subject's entire weight while the subject is in the first position, while the subject is in the second position and while the subject is performing the mobility task moving from the first position to the second position, each support surface having a non-overlapped area at least large enough to accommodate a foot of the subject;

computational means for accepting the output signals from the force-sensing means and calculating the total magnitude of the forces exerted by the subject on the support surfaces; and display means for displaying the total magnitude of the forces and for displaying as a performance goal a trajectory of the total magnitude of forces over time representative of a normally coordinated and balanced subject performing the mobility task moving from the first position to the second position.

23. An apparatus according to claim 22, wherein the forces have a center of force on the sensing area;

wherein the computational means includes means for calculating the center of force exerted by the subject on the support surfaces; and wherein the display means includes means for displaying the movement of the center of force calculated by the computational means and for displaying as an additional performance goal a trajectory of the center of force representative of a normally coordinated and balanced subject performing the mobility task moving from the first position to the second position.

24. An apparatus according to claim 23, wherein the support surfaces are arranged so that the subject may be in contact with a different support surface in the second position from the support surface in contact with the subject in the first position.

25. An apparatus according to claim 24, wherein the support surfaces have markings indicating preferred positions where the subject should place a part of the subject's body while in the first position and while in the second position.

26. An apparatus according to claim 24, wherein the force-sensing means includes a forceplate, wherein the forceplate has a top surface;

wherein one of the support surfaces is a first surface which is parallel to and spaced away from the forceplate's top surface and which is smaller than the sensing area of the force-sensing means so that a portion of the forceplate's top surface is not overlapped by the first surface; and wherein a second support surface is the portion of the forceplate's top surface not overlapped by the first surface.

27. An apparatus according to claim 24, wherein the force-sensing means is a forceplate and the plurality of support surfaces includes a staircase-like series of non-overlapping surfaces parallel with one another and the forceplate's top surface and at progressively greater distances above the forceplate's top surface.

28. An apparatus according to claim 23, wherein the support surfaces are arranged so that the subject may be in contact with different areas of the support surfaces in the second position from the areas of the support surface in contact with the subject in the first position.

29. An apparatus according to claim 28, wherein the support surfaces have markings indicating preferred positions where the subject should place a part of the subject's body while in the first position and while in the second position.

30. An apparatus according to claim 28, wherein the force-sensing means includes a forceplate, wherein the forceplate has a top surface;

wherein one of the support surfaces is a first surface which is parallel to and spaced away from the forceplate's top surface and which is smaller than the sensing area of the force-sensing means so that a portion of the forceplate's top surface is not overlapped by the first surface; and wherein a second support surface is the portion of the forceplate's top surface not overlapped by the first surface.

31. An apparatus according to claim 30, wherein the force-sensing means is a forceplate and the plurality of support surfaces includes a staircase-like series of non-overlapping surfaces parallel with one another and the forceplate's top surface and at progressively greater distances above the forceplate's top surface.

* * * * *